United States Patent
Molino et al.

(10) Patent No.: US 6,911,050 B2
(45) Date of Patent: Jun. 28, 2005

(54) PROSTHETIC KNEE UNIT

(76) Inventors: Joseph L. Molino, 2 Aura Dr., Valley Cottage, NY (US) 10989; Michael Rebarber, 28 Buckingham Pl., Glen Rock, NJ (US) 07452

( * ) Notice: Subject to any disclaimer, the term of this patent is extended or adjusted under 35 U.S.C. 154(b) by 142 days.

(21) Appl. No.: 10/278,361

(22) Filed: Oct. 23, 2002

(65) Prior Publication Data

US 2004/0083008 A1 Apr. 29, 2004

(51) Int. Cl.$^7$ ............................... A61F 2/64; A61F 2/68
(52) U.S. Cl. ........................... 623/43; 623/45; 188/297; 188/304
(58) Field of Search ............................. 623/27, 39–46; 188/294, 297, 304

(56) References Cited

U.S. PATENT DOCUMENTS

| | | | |
|---|---|---|---|
| 2,605,474 A | | 8/1952 | Oliver |
| 4,212,087 A | * | 7/1980 | Mortensen .................... 623/26 |
| 5,092,902 A | | 3/1992 | Adams et al. |
| 5,376,137 A | | 12/1994 | Shorter et al. |
| 5,383,939 A | * | 1/1995 | James .......................... 623/24 |
| 5,405,409 A | | 4/1995 | Knoth |
| 5,779,735 A | | 7/1998 | Molino |
| 6,113,642 A | * | 9/2000 | Petrofsky et al. .............. 623/24 |
| 6,187,052 B1 | | 2/2001 | Molino et al. |
| 6,517,585 B1 | * | 2/2003 | Zahedi et al. ................. 623/24 |
| 6,613,097 B1 | * | 9/2003 | Cooper .......................... 623/44 |

FOREIGN PATENT DOCUMENTS

| | | |
|---|---|---|
| DE | 724959 | 9/1942 |
| DE | 1 075 277 | 10/1952 |
| DE | 1 906 284 | 9/1970 |
| DE | 36 03 467 A 1 | 8/1986 |
| DE | 693 12 771 T 2 | 12/1992 |
| DE | 43 05 213 A 1 | 8/1993 |
| DE | 42 33 247 A 1 | 4/1994 |
| DE | G 94 05 545.9 | 8/1994 |
| DE | 44 10 730 C 1 | 6/1995 |
| DE | 196 21 034 A | 12/1996 |
| GB | 2 331 018 B | 9/1999 |
| GB | 2367 753 | 4/2002 |
| WO | WO 92/22267 | 12/1992 |

* cited by examiner

*Primary Examiner*—Bruce Snow
(74) *Attorney, Agent, or Firm*—Lawrence G. Fridman (57) ABSTRACT

A prosthetic knee device having a hydraulic cylinder with a piston and a gas cylinder. A connecting element extends outwardly from the piston and passing through a gas cylinder. A bottom portion of the gas cylinder is adapted for slidable engagement with the hydraulic cylinder. A plunger is fixedly connected to the hydraulic cylinder. An outer periphery of a plunger is adapted for slidable engagement with the interior surface of the gas cylinder, so as to form an operational chamber within the gas cylinder between the bottom portion thereof and the plunger. The operational chamber is responsive to the movement of the prosthetic knee device.

21 Claims, 6 Drawing Sheets

PROSTHETIC KNEE UNIT

BACKGROUND OF THE INVENTION

1. Field of the Invention

This invention relates to prosthetic devises in general and, more particularly, it relates to a knee unit for a prosthetic leg.

2. Description of the Prior Art

One of the primary problems in providing a satisfactory above-knee prosthetic leg involves controlling of the swing phase of the walking cycle, including the terminal impact and the extension cycle regarding its speed and intensity. The terminal impact is known to be the resultant force generated during the swinging motion of a lower limb and an upper limb with respect to each other, when the prosthetic leg reaches the end of its swing phase, prior to achieving a substantially straight position. When humans advance in the walking cycle, a leg bends at the knee and is lifted above the ground. In order to be supported by the ground again, the leg has to be fully extended. Prosthetic legs operate in a similar manner. Furthermore, if the motion of the prosthetic lower limb caused by the forces of the terminal impact is not decelerated, a very revealing and often embarrassing noise is produced. To the discomfort of a patient, this makes the presence of the prosthesis very obvious, causing other people to be aware that the patient has an artificial leg. The terminal impact also negatively affects the structural elements of the prosthetic device itself, often leading to their damage. All of these emphasize the necessity of minimizing the effect of the terminal impact.

Another negative aspect of the prior art prosthetic devices is the artificially high rate at which the leg advances during the swing phase to its complete straight position. This is quite different from a normal leg which slows down at the end of the travel. The swing phase of the walking cycle causes the leg to accelerate in its motion from being bent to being straight. At the beginning of the swing phase, the normal leg moves rapidly, so that it can be situated underneath the patient's body. At the end of the swing phase the leg typically slows down. In the prosthetic devices, in the process of reaching the stop in full extension, an undesirable momentum of forces develops which has to be slowed down or minimized. If such momentum is not minimized, one part of the leg will crash against the other part of the leg. The prior art prosthetic knee devices typically utilize hydraulic-based systems for their operations. In view of the presence of the liquid mediums (such as oil, etc.), which are difficult to compress, the prosthetic devices move at a substantially constant rate during the entire walking cycle. Therefore, the highly desirable deceleration of the movement of the prosthetic leg at the end of the travel is not typically provided. Thus, there is an obvious need for a prosthetic device capable of regulating and decelerating its motion during the swing phase before it reaches a substantially straight position.

Various hydraulically operated knee units for above-knee prosthetic legs are known in the prior art. However, even sophisticated knee units, as disclosed, for example, by the inventor's own U.S. Pat. No. 5,779,735 do not provide prosthetic devices capable of efficiently avoiding the terminal impact, and slowing down the motion of the limbs prior to the leg reaching substantially straight position. All of these problems are substantially alleviated in the prosthetic knee device of the invention which utilizes the compressible nature of gas or air for negating the undesirable forces. The prosthetic device of the invention closely simulates the movement of human limbs, without being subjected to the results of the terminal impact. It moves rapidly in the initial stages of extension, and then slows down before reaching the stop in full extension.

SUMMARY OF THE INVENTION

One aspect of the invention provides a prosthetic device having an upper prosthetic limb member, a lower prosthetic limb member, a hydraulic cylinder and a gas cylinder. A piston is movably disposed inside of the hydraulic cylinder and an upper prosthetic limb member is associated with the piston. A bottom portion of the gas cylinder is adapted for slidable engagement with the hydraulic cylinder. A plunger is connected to the hydraulic cylinder in such a manner that an outer periphery thereof is adapted for slidable engagement with the interior surface of the gas cylinder. An operational chamber is formed within the gas cylinder between the bottom portion and the plungers. The operational chamber is responsive to operation of the prosthetic leg in such a manner that during downward movement of the upper prosthetic limb member and the external cylinder, the operational chamber is expanded, whereas during the upward movement thereof the operational chamber is being reduced so as to compress and discharge a gas accumulated thereinside.

Another aspect of the invention provides a prosthetic device in which the plunger is fixedly connected to an upper region of the hydraulic cylinder. The piston is connected to the upper prosthetic limb member by a connecting element which passes through and is fixedly attached to the upper region of the gas cylinder. The gas is discharged from the operational chamber in a controlled manner, so as to prevent an excessive rate of motion of the device and an excessive terminal impact.

According to a further aspect of the invention the bottom portion of the gas cylinder is formed with a central opening and an upwardly directed engaging member which extends about the periphery of the opening, so as to slidably engage an exterior portion of the hydraulic cylinder. A downwardly directed engaging member is situated at an outer periphery of the plunger and is adapted for slidable engagement with the inner surface of the gas cylinder.

As to still another aspect of the invention, a valve arrangement is provided within the operational chamber, so that upon downward motion of the upper prosthetic limb member, the operational chamber is expanded to allow the gas to enter the operational chamber. During upward motion of the upper prosthetic limb member, the gas cylinder moves upward diminishing the operational chamber, so as to compress the gas situated thereinside. The valve arrangement is situated in the operational chamber in the vicinity of the bottom portion of the gas cylinder and provides communication between the operational chamber and an outside environment.

As to a still further embodiment of the invention, a prosthetic knee is provided having a hydraulic cylinder, a connecting element and a gas cylinder. A piston is movably disposed within the hydraulic cylinder and the connecting element extends outwardly from the piston. The gas cylinder is formed by at least interior and exterior surfaces and extends between top and bottom portion thereof. A bottom portion of the gas cylinder is adapted for slidable engagement with the hydraulic cylinder. The plunger is fixedly connected to the hydraulic cylinder and an outer periphery of the plunger is adapted for slidable engagement with the interior surface of the gas cylinder, so as to form an operational chamber within the gas cylinder between the bottom portion and plungers. The operational chamber is responsive to upward and downward movement of the gas cylinder.

As to still another aspect of the invention, in the prosthetic knee the plunger is fixedly connected to an upper region of the hydraulic cylinder. The connecting element passes through and is fixedly connected to an upper region of the gas cylinder. The bottom portion of the gas cylinder is formed with a central opening and an upwardly directed engaging member which extends about the periphery of the opening and slidably engages an exterior portion of the hydraulic cylinder. A downwardly directed engaging member is situated at an outer periphery of the plunger and is adapted for slidable engagement with the inner surface of the gas cylinder. A valve arrangement is provided within the operational chamber, so that upon expansion of the operational chamber it allows the gas to enter the operational chamber. Upon contraction of the operational chamber, the gas is discharged from the operational chamber via the valve arrangement.

BRIEF DESCRIPTION OF THE DRAWINGS

The preferred embodiment of the invention will hereinafter be described in conjunction with the appended drawings provided to illustrate and not to limit the invention, and in which.

DETAILED DESCRIPTION OF THE INVENTION

Figure 1:
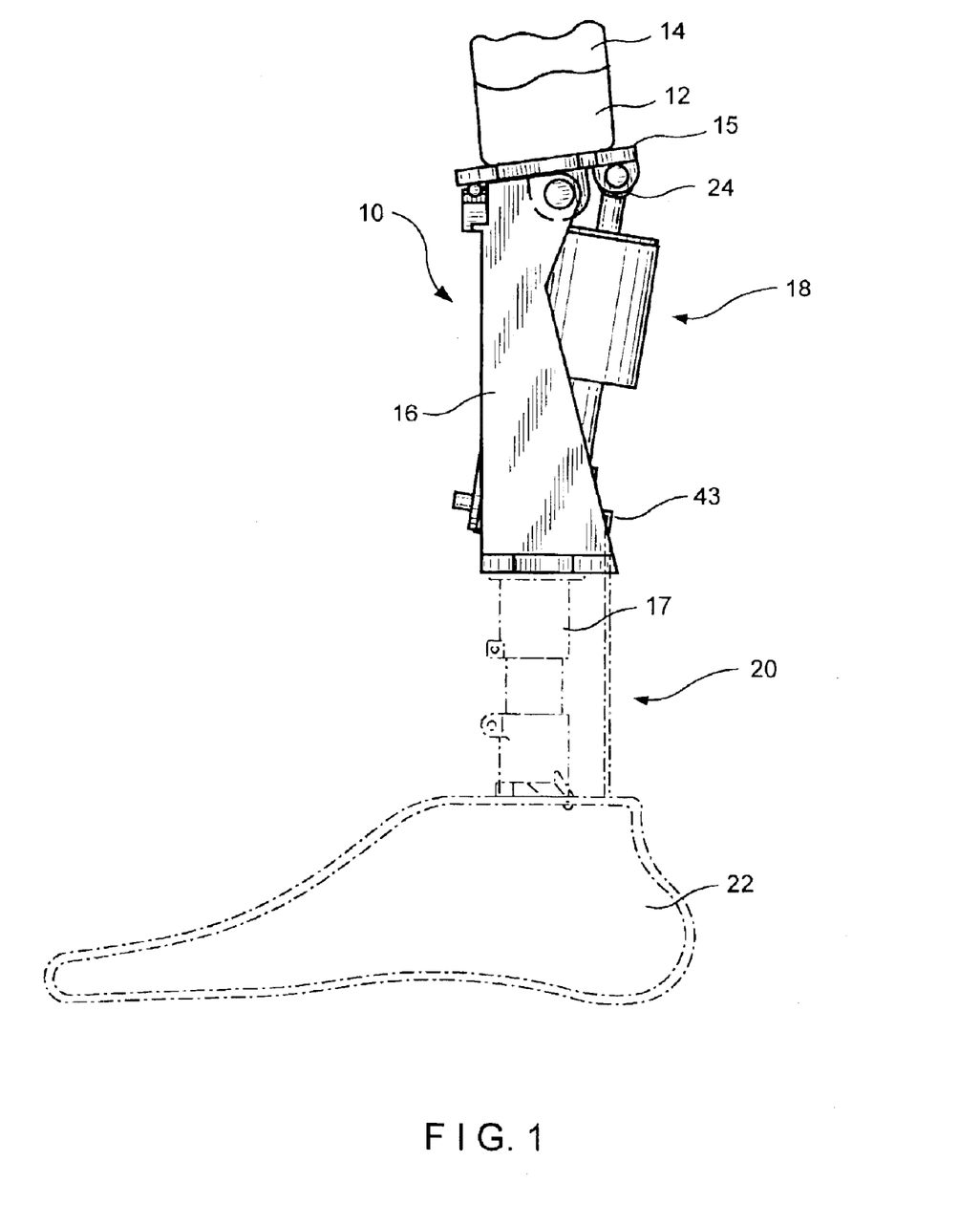
FIG. 1 is a diagrammatic representation generally illustrating an above-knee prosthetic leg incorporating a prosthetic knee device of the invention.

Referring now to FIG. 1, in which an above-knee prosthetic leg is designated generally by the numeral 10 and which includes a socket or an upper prosthetic limb member 12 adapted for receiving a leg stump 14 of an amputee. The socket 12 is coupled by conventional means to an adjustable table 15 provided at the top portion of the knee cage 16, which supports a knee control unit 18. The table 15 is adapted for pivotal motion relative to the cage upright. A pylon 17 at one end is coupled to the bottom of a knee cage 16 and at the other end is coupled to a prosthetic foot 22. The pylon 17 and prosthetic foot 22 define a lower prosthetic limb member 20.

Figure 2:
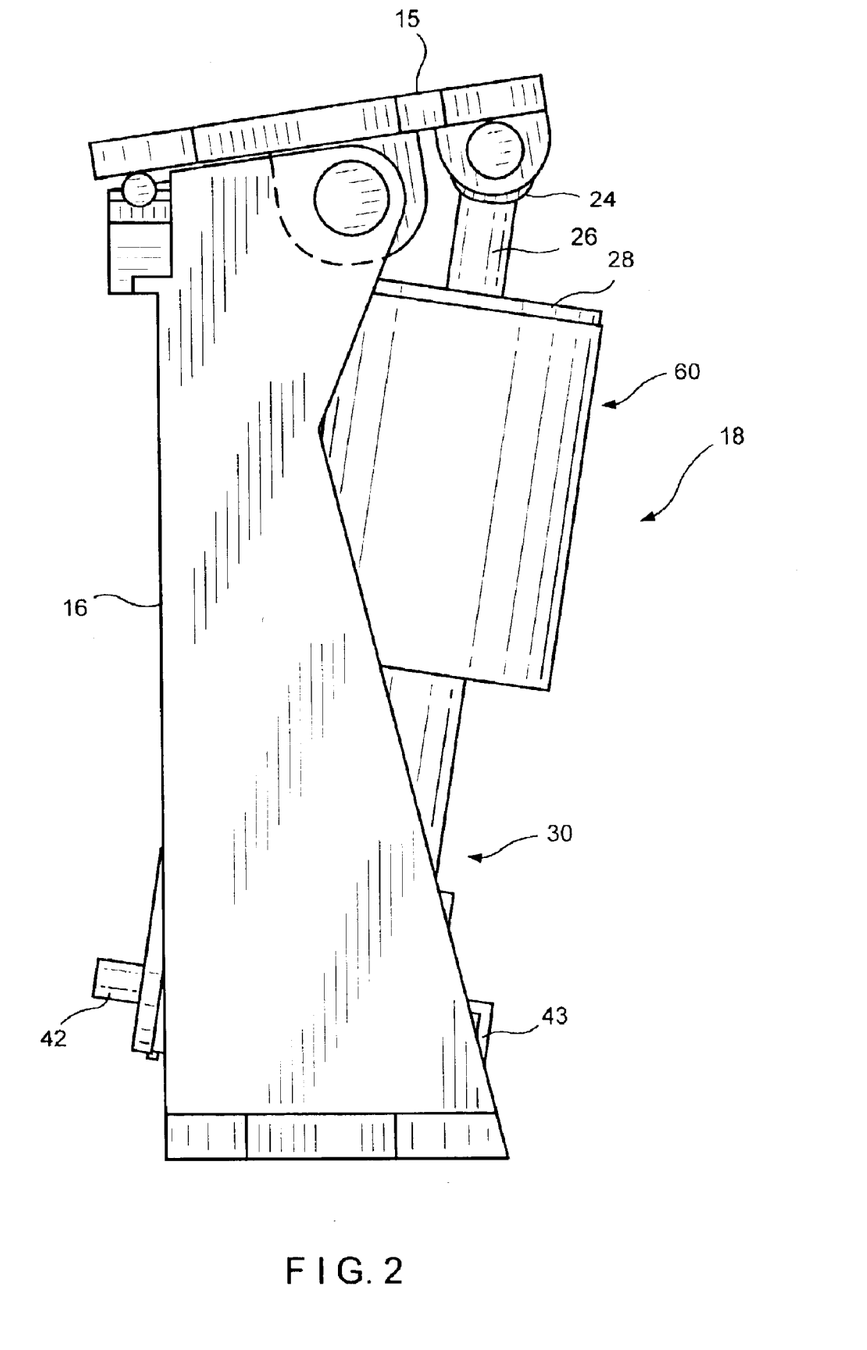
FIG. 2 is a general view showing the prosthetic knee device.
Figure 3:
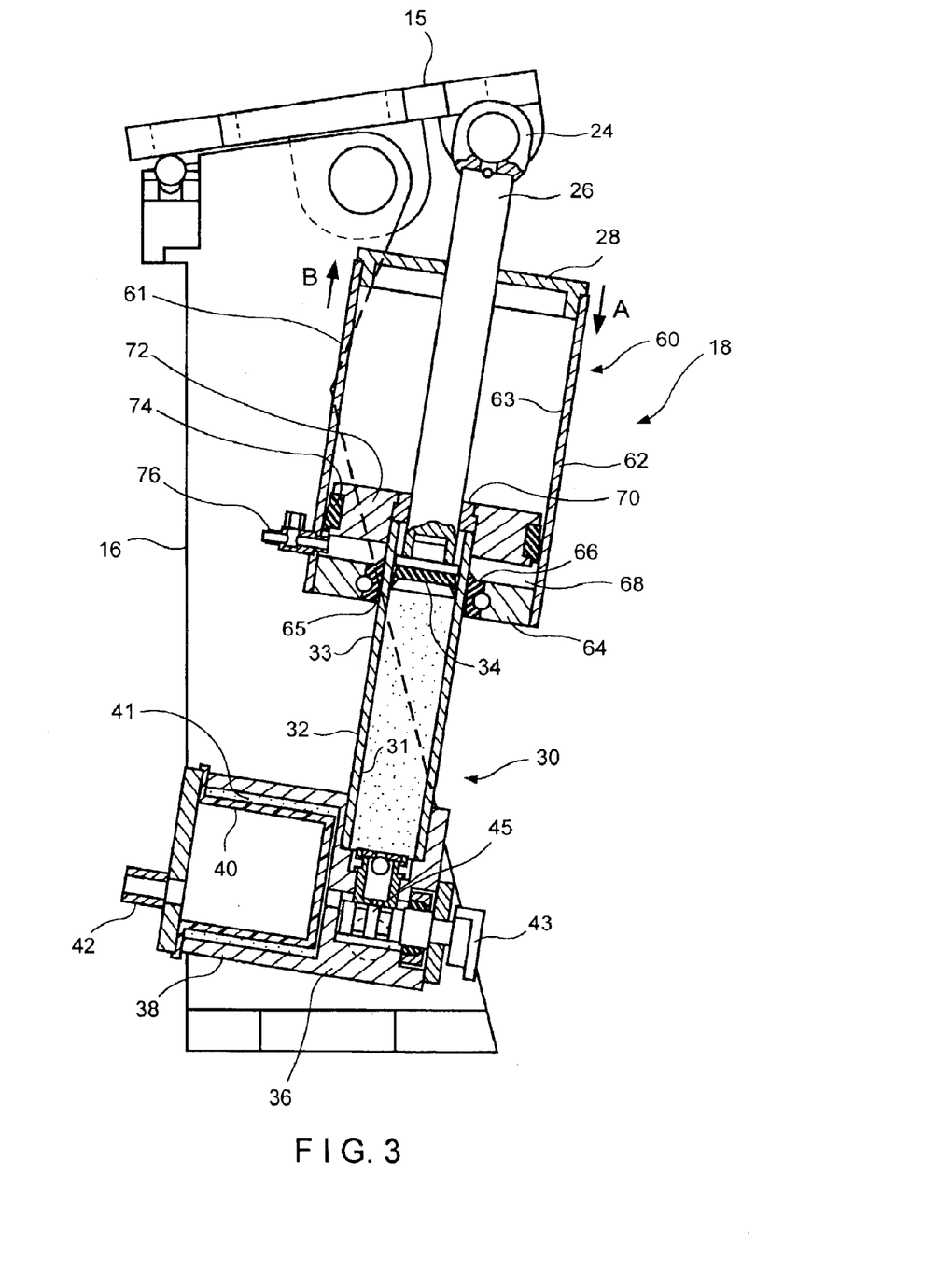
FIG. 3 is a partial section view of the prosthetic knee device of the invention.

As best illustrated in FIGS. 1–3, the improved knee assembly of the invention is positioned within the cage 16 and consists of a gas or air cylinder unit 60, the hydraulic cylinder unit 30, a control valve-bladder sub-assembly, etc. A pivot mount 24 is provided for coupling the knee control unit 18 of the invention to the cage 16. A hydraulic cylinder 30 is formed by a substantially cylindrical wall 32 having inner and outer surfaces 31 and 33 respectively and contains therein a piston 34 which is displaced by a suitable fluid which may be, for purposes of illustration, a silicone oil. A valve body 36 is coupled to the cylinder 30 and supports a flow control valve.

Figure 4:
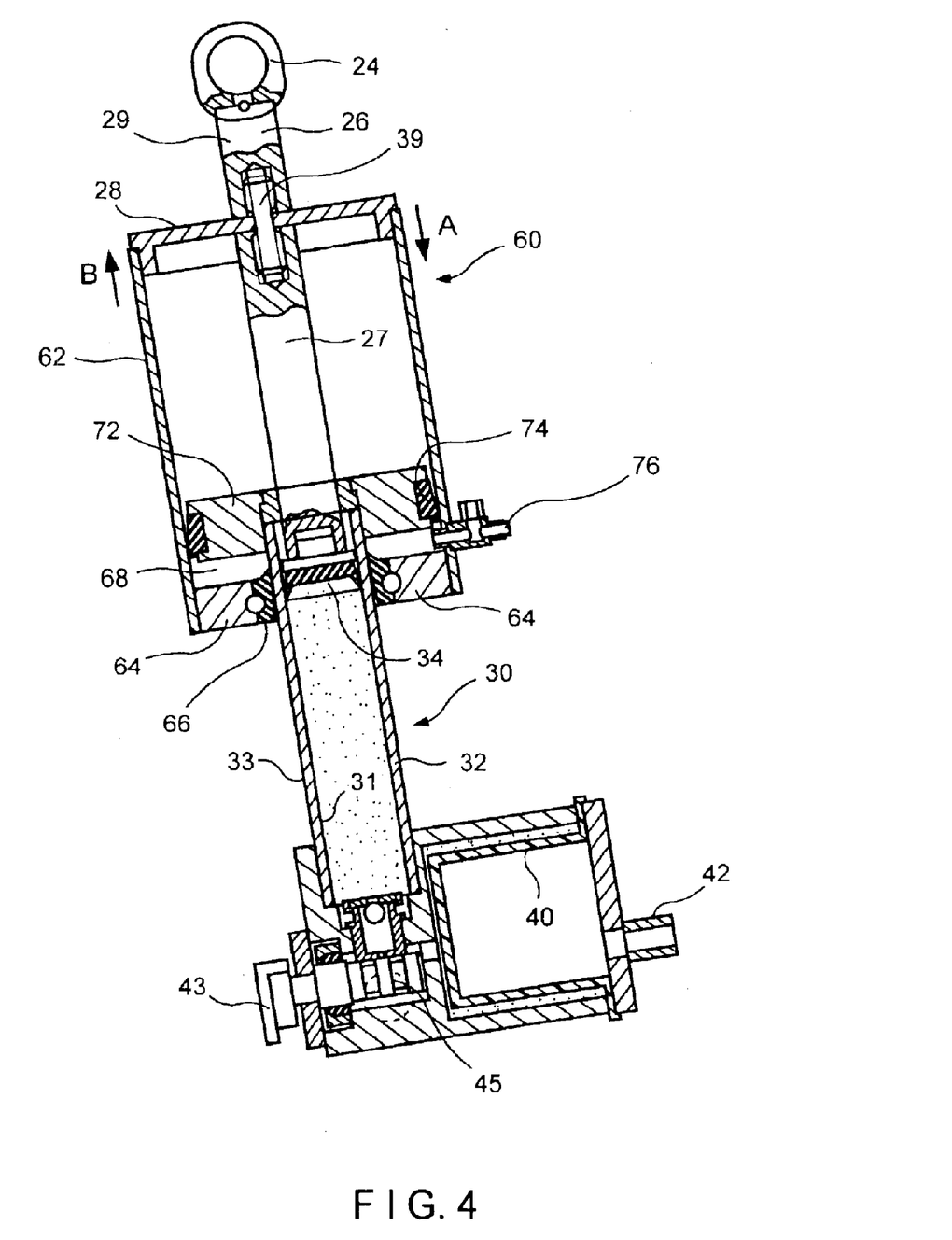
FIG. 4 is another section view showing the prosthetic knee device with an operational chamber in a retracted condition.
Figure 5:
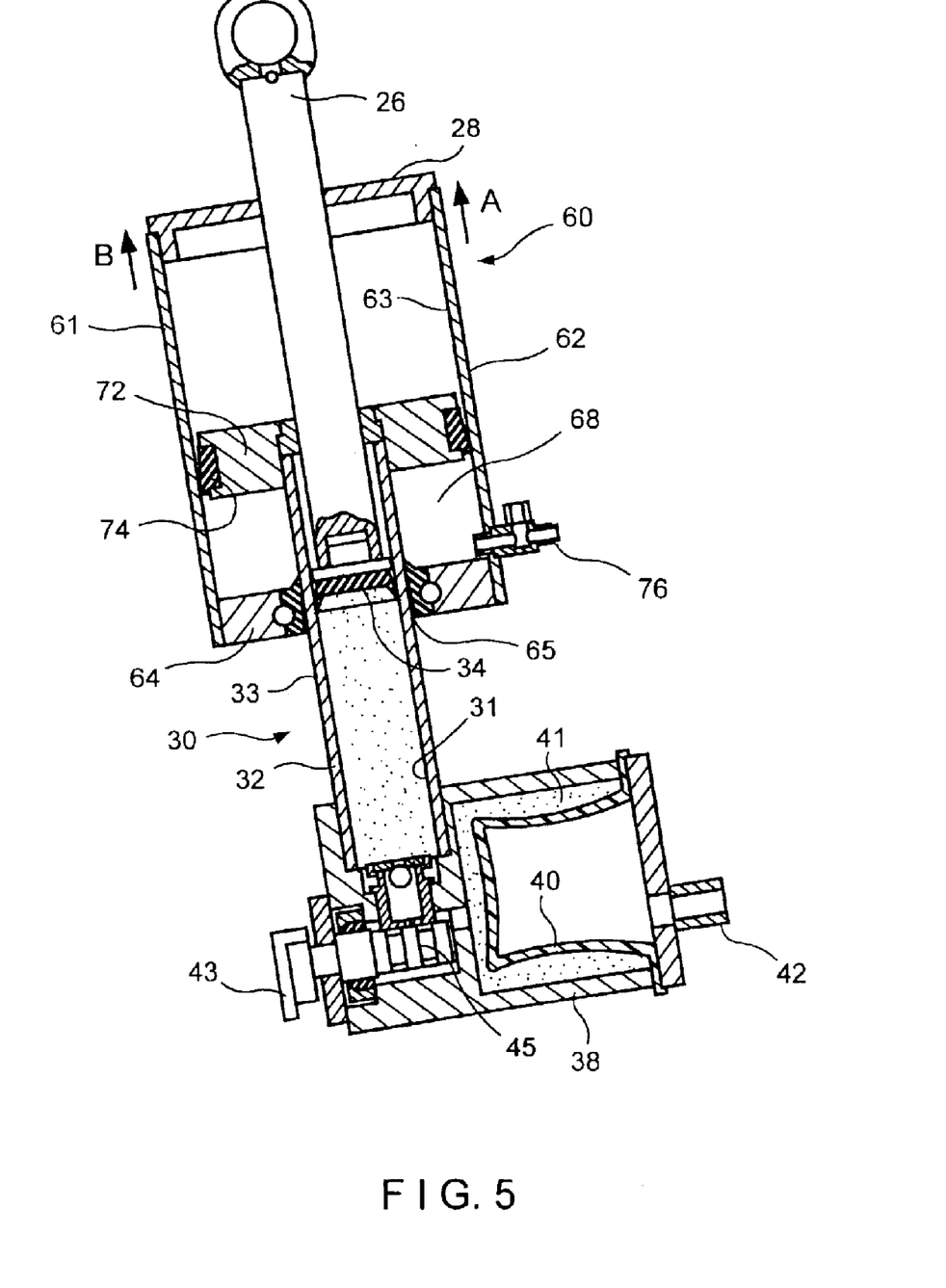
FIG. 5 is a section view of the prosthetic knee device showing the operational chamber in a semi-retracted condition.
Figure 6:
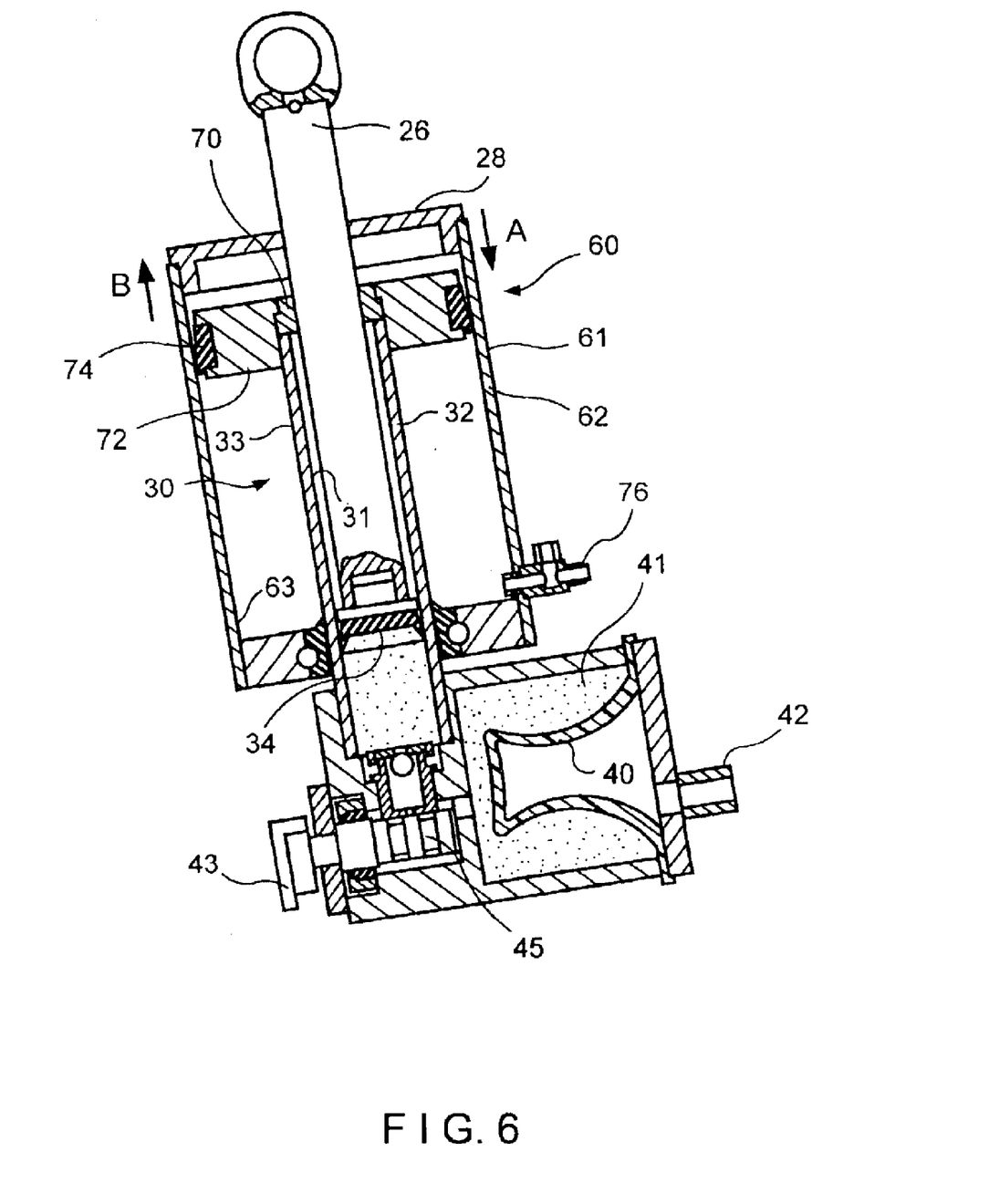
FIG. 6 is a section view showing the operational chamber in an expanded condition.

The gas cylinder unit 60 is formed with a substantially cylindrical housing 62 having exterior 61 and interior 63 surfaces. A closing cap 28 is provided at the top of the gas cylinder 60. A connecting element or piston rod 26 is pivotably connected to the table 15 of the cage at the pivot mount 24 and extends between the cage and a piston 34 of the hydraulic cylinder 30. The connecting element 26 at one end passes through the cap 70 positioned at the top region of the hydraulic cylinder 30, whereas at the other end it passes through and is fixedly attached to the gas cylinder 60 at an aperture formed in a central part of the closing cap 28. In one embodiment of the invention, as best illustrated in FIGS. 3, 5 and 6, the connecting element 26 is in the form of a unitary member. On the other hand, as shown in FIG. 4, the connecting element 26 can be in the form of two independent members 27 and 29 interconnected by a threaded rod 39 in such a manner that the closing cap 28 is sandwiched between these two members.

A bottom portion 64 of the gas cylinder 60 is in the form of a flexible seal or membrane formed with a central opening 65. An upwardly oriented engaging member 66 extends circumferentially about the opening 65, so as to be concentric with and slidably engage the exterior surface 33 of the hydraulic cylinder 30. This arrangement provides a gas impermeable slidable connection between the flexible bottom portion 64 of the gas cylinder including the engaging member 66 and the exterior surface 33 of the hydraulic cylinder 30 which are movable with respect to each other.

The receiving arrangement or cap 70 provided at the top area of the main hydraulic cylinder 30 is adapted to fixedly receive and accommodate a plunger or interior compression seal 72. A downwardly directed engaging member 74 is situated at an outer periphery of the plunger 72 and adapted for slidable engagement with the inner surface 63 of the gas cylinder 60. An operational chamber 68 is formed within the inner space of the gas cylinder 60 between the opposing bottom portion 64 and plunger 72.

A valve arrangement 76 is disposed within the wall of the gas cylinder 60, so as to provide communication between the operational chamber 68 and outside environment. Thus, in the preferred embodiment of the invention an outside air is used for the operation of the operational chamber 68. Nevertheless, it should be noted that utilization of any suitable source of gas for the same purpose is also contemplated. The valve arrangement 76 is preferably positioned within the gas cylinder 30, slightly above the bottom portion thereof 64. The valve arrangement 76 can be adjusted to regulate flow of gas or air in and out of the operational chamber 68. It will be discussed hereinbelow that during the movement of the gas cylinder 60 in one direction the valve arrangement 76 is adapted to controllably discharge the gas accumulated within the operational chamber 68, whereas during the movement of the gas cylinder 30 in the opposite direction it operates as a control valve introducing air or gas into the expanding operational chamber 76.

The plunger 72 and the bottom portion 64 of the gas cylinder forming the operational chamber 68 can be made of a semi-resilient material such as Teflon and can be spring loaded so as to be pushed either inward or outward. The flexible plunger or seal 72 can be provided with an internal spring pushing it outward. On the other hand, the flexible bottom portion 64 of the gas cylinder can be formed with an outside spring that compresses the bottom portion against the exterior surface 33 of the hydraulic cylinder 30. Such arrangement is resulted in a positive seal around the exterior surface 33 of the hydraulic cylinder.

In certain embodiments it is recommended to place a seal underneath the cap 70 provided at the upper region of the hydraulic cylinder 30. This seal prevents gas or air penetration into the hydraulic fluid situated within the hydraulic cylinder 30 and prevents formation of an undesirable gas-oil mixture. This is especially important in the condition of relatively high pressure developed within the operational chamber 68. A positive seal should be preferably maintained between the hydraulic region and the gas region of the prosthetic knee unit, i.e. between the gas cylinder 60 and the hydraulic cylinder 30. This is achieved by providing a seal underneath the plunger 72, which also prevents migration of a gas into the hydraulic region.

Operation of the check valve 45 and the rotary cam 43 do not form an essential part of the present invention and have been in full detail discussed by U.S. Pat. No. 5,779,735 which the present application incorporates by reference. Similar to the prosthetic knee disclosed by U.S. Pat. No. 5,779,735, a bladder membrane 40 is situated within bladder cylinder 38 which includes a bladder valve 42. The valve 42 is adjustable for varying bladder compression, flexion resistance and extension drive. The bladder 40 is affected by the operation of valves situated within the valve body 36 (not shown), so as to be compressed for storing all of the required energy. The bladder is capable of storing the kinetic energy for the return cycle or the upward motion of the piston 34. This enables the hydraulic fluid to be moved from the bladder chamber 41 into the hydraulic cylinder 30 to have the required resistance within the cylinder 30 when the bladder collapses. Such action accumulates and stores the kinetic energy required for the operation of the knee unit of the invention.

An accumulation chamber 41 with a bladder cylinder 38 accommodates the displaced oil. As the oil is displaced during a compression stroke, pressure is exerted on the bladder membrane 40 allowing it to compress the gas situated thereinside and accept the displaced oil. Pressure is increased on the inner area of the bladder membrane 40, thus storing enough kinetic energy to power the return cycle and return of the piston 34 to the extended position. The air valve 42 communicating with the airside of the bladder chamber can adjust the level of kinetic energy. The force necessary to compress and extend the piston 34 and piston rod or connecting element 26 is adjustable by increasing or decreasing the amount of air pressure in the bladder cylinder 38. During operation of the knee the kinetic energy is stored in the bladder capable of driving piston 34.

A cartridge-type ball check valve 45 is placed between the hydraulic cylinder 30 and the bladder chamber 41. To stop the flow of fluid from the cylinder 30 to the bladder chamber 41 a rotary cam 43 associated with the ball check valve 45 is provided. As the cam is rotated the ball is lifted or lowered into the ball seat either allowing or not allowing passage of fluid through the ball seat to the accumulation chamber. Free oil flow is allowed back into the cylinder 30 due to the kinetic energy stored in the compressed air/gas in the bladder chamber 41 pushing on the bladder 40 to return the oil to the hydraulic cylinder 30 through the check valve 45 to the cylinder returning the cylinder to the extended position.

In operation (see FIGS. 3–6), as the table 15 of the cage 16 is either flexed or extended, the gas cylinder 60, which is fixedly associated with the piston rod or connecting element 26, is allowed to move in the directions identified by the arrows A and B away or toward the lower prosthetic limb member 20. In this respect, when the table 15 and the gas cylinder 60 are moved in the direction of the lower prosthetic limb member or the arrow A, the operational chamber 68 is expanded allowing gas to enter and accumulate in the space between the bottom portion 64 and the plunger 72. This occurs by means of the valve arrangement 76, which in this mode operates in the exterior to the interior direction. Upon extension of the leg, the table 15 of the cage 16 and the gas cylinder 60 move away from the lower prosthetic limb member 20 or in the direction of the arrow B. In these circumstances, the space of the operational chamber 68 between the elements 64 and 72 decreases. This causes gradual compression of the gas within the operational chamber 68, resulted in the increased resistance to the upward movement of the connecting element 26 and the table 15. Thus, the motion of the table 15 of the cage and the upper limb member associated therewith are being slowed down by the action of the compressed gas, controlling extension of the prosthetic leg. Upon further compression, the gas is allowed to escape in a controlled manner from the operational chamber 68 through the valve arrangement 76. This in turn slows down the extension cycle and prevents the excessive rate of the leg motion during the swing phase. Furthermore, the undesirable forces and consequences of the terminal impact are minimized and become manageable.

More specifically, the prosthetic device of the invention uses the kinetic energy that is stored in the bladder 40 to provide the upward movement of the piston 34 and the respective motion of the connecting element or piston rod 26. This motion, in view of the permanent connection between the connecting element 26 and the gas cylinder 60, is translated into the upward motion of the latter. Furthermore, in operation, as the pivot mount 24 and the connecting element or piston rod 26 along with the outside gas cylinder 60 are also moved upward or in the direction of the arrow B, the bottom portion 64 of the gas cylinder with upwardly directed engaging member 65 also slide in this direction along the outer wall 33 of the hydraulic cylinder 30. During this action the gas is trapped within the operational chamber 68, and is pressed against the stationery plunger 72 having the downwardly directed engaging member or lip 74. This causes compression of the gas accumulated within the operational chamber 68. As the space of the operational chamber diminishes during the further motion of the gas cylinder 60 in the direction of the arrow B, the compressed gas between the bottom portion 64 and the plunger 72 is discharged in a controlled manner through the gas bleeding valve arrangement 76. In this operational mode, the valve arrangement 76 operates in the interior to the exterior direction.

To summarize the above, as the leg is extended, and the upwardly directed forces are exerted on the above discussed elements, the gas cylinder 60 also moves upwardly or in the direction of the upper prosthetic limb member. This motion causes compression of the gas within the operational chamber 68. Initially, due to the compressible nature of gas or air, resistance to such motion of the gas cylinder 60 is minimal. This situation exists until the arrangement reaches the point prior to the terminal impact. At this moment, the gas within the operational chamber 68 is substantially compressed, so that further upward motion of the gas cylinder 60 meets greater resistance. As a result, the movement of the lower prosthetic limb member is decelerated, substantially avoiding the terminal impact.

In the down stroke, when the downwardly directed forces are applied by the upper prosthetic limb member 12, through the table 15 and the connecting element 26, the gas cylinder 60 moves in the direction of the arrow A or toward the lower prosthetic limb member 20. At the end of this motion, when the gas cylinder 60 reaches its fully extended position, the operational chamber 68 is filled with gas or air. In this mode the valve arrangement 76 acts as a check valve providing communication in the exterior to interior direction, so as to allow the rapid influx of an ambient air into the operational chamber 68.

Actuation of the cam valve 45 in the knee control unit 18 is associated with at least one of the following three modalities. One mode of operation is mechanical in nature and operates by providing a connection between the knee and a movable ankle or foot. When the foot is in planter flexion or when the ankle position allows planter flexion of the foot, a connector or cable pulls on the cam lever arm 43 which locks the cam valve 45 into a closed position preventing flexion of the knee. As the leg is brought into a vertical position, the cam valve 45 is placed into an open position, thereby allowing the flow of fluid from the hydraulic cylinder 30 into the bladder chamber 41.

The knee control unit 18 of the invention is also adaptable for operation in the electromechanical mode, whereby a switch located on the plantar surface of the foot or the bottom surface of the foot can be activated. Such activation elicits a response from a survo to pull the cam actuating arm 43 into a position in which the foot contacts the floor. The cam valve 45 is allowed to be placed into a position facilitating the drop of the ball into the seat, so as to seal the unit. Such action prevents flow of the fluid through the control unit 18 leading to complete stoppage of the flexion-ability of the knee.

A further mode of controlling the knee is by means of myoelectric control. In this mode a signal from the residual musculature, or an electronic signal from the brain of a patient to the residual musculature is amplified and sent to a discriminator circuit. There the signal is analyzed to define the type of signal in terms of its amplitude and duration. After that another discrimination step can be conducted to define a selected response mode or activity such as walking, climbing stairs, descending stairs, seating, etc. The proper placement of the cam valve 45 is elicited by an arrangement utilizing a signal from the discriminator circuit. This provides a measured travel, so as to place the cam valve 45 in a desired position, in order to coincide with the motion that is elicited by the brain. This is necessary to achieve one of the previously discussed activities.

What is claimed is:

1. A prosthetic knee, comprising:
   a hydraulic cylinder having a piston movably disposed thereinside;
   a connecting element extending outwardly from said piston;
   a gas cylinder formed by at least interior and exterior surfaces and extending between top and bottom portions thereof, a bottom portion of the gas cylinder is adapted for slidable engagement with said hydraulic cylinder; and
   a plunger fixedly connected to said hydraulic cylinder, an outer periphery of the plunger is adapted for slidable engagement with said interior surface of the gas cylinder, so as to form an operational chamber within said gas cylinder between said bottom portion and said plunger, said operational chamber being responsive to movements of said gas cylinder.

2. The prosthetic knee according to claim 1, wherein said plunger is fixedly connected to an upper region of the hydraulic cylinder.

3. The prosthetic knee unit according to claim 1, wherein said bottom portion of the gas cylinder and said plunger are made of a semi-resilient material and said valve arrangement provides communication between the operational chamber and an outside environment and said gas is an ambient air.

4. The prosthetic knee according to claim 1, wherein said connecting element passes through and is fixedly connected to an upper region of the gas cylinder.

5. The prosthetic knee device according to claim 4, further comprising said bottom portion of the gas cylinder is formed with a central opening, an upwardly directed engaging member extends about the periphery of said opening, so as to slidably engage an exterior portion of said hydraulic cylinder.

6. The prosthetic knee according to claim 5, further comprising a downwardly directed engaging member situated at an outer periphery of said plunger said engaging member is adapted for slidable engagement with said inner surface of the gas cylinder.

7. The prosthetic knee according to claim 6, further comprising a valve arrangement provided within said operational chamber, so that upon expansion of said operational chamber the gas enters said operational chamber via said valve arrangement and upon contraction of said operational chamber the gas is compressed within said operational chamber and discharged therefrom via said valve arrangement.

8. The prosthetic knee according to claim 6, wherein said valve arrangement is situated in the operational chamber in the vicinity of the bottom portion of the gas cylinder.

9. The prosthetic knee according to claim 6, wherein upon motion of the gas cylinder away from said hydraulic cylinder the operational chamber is reduced compressing and discharging the gas situated thereinside.

10. The prosthetic knee according to claim 6, wherein upon motion of the gas cylinder toward the hydraulic cylinder the operational chamber is expanded.

11. A prosthetic device, comprising:
    an upper prosthetic limb member;
    a lower prosthetic limb member;
    a hydraulic cylinder defined by exterior and interior portions and having a piston movably disposed thereinside;
    said upper prosthetic limb member being associated with said piston;
    a gas cylinder formed by at least interior and exterior surfaces and extending between top and bottom portions thereof, a bottom portion of the gas cylinder is adapted for slidable engagement with said hydraulic cylinder; and
    a plunger fixedly connected to said hydraulic cylinder, an outer periphery of the plunger is adapted for slidable engagement with said interior surface of the gas cylinder, so as to form an operational chamber within said gas cylinder between said bottom portion and plunger;
    whereby said operational chamber being responsive to operation of said prosthetic leg.

12. The prosthetic device according to claim 11, wherein during movement of said piston and said gas cylinder toward said lower prosthetic limb member the operational chamber is expanded.

13. The prosthetic device according to claim 12, further comprising a downwardly directed engaging member situated at an outer periphery of said plunger, said downwardly directed engaging member is adapted for slidable engagement with said inner surface of the gas cylinder.

14. The prosthetic device according to claim 13, further comprising a valve arrangement provided within said operational chamber, during downward motion of the upper prosthetic limb member said operational chamber is expanded, so as to allow a gas to enter said operational chamber via said valve arrangement.

15. The prosthetic device according to claim 14, wherein upon upward motion of the upper prosthetic limb member said gas cylinder moves in the same direction diminishing the operational chamber, so as to compress and discharge said gas from said operational chamber via said valve arrangement.

16. The prosthetic device according to claim 15, wherein said valve arrangement provides communication between the operational chamber and an outside environment and said gas is an ambient air.

17. The prosthetic device according to claim 14, wherein said valve arrangement is situated within the operational chamber in the vicinity of said bottom portion of the gas cylinder.

18. The prosthetic device according to claim 11, wherein during movement of said piston and said gas cylinder away from said lower prosthetic limb member said operational chamber is reduced so as to compress a gas accumulated thereinside.

19. The prosthetic device according to claim 18, further comprising said bottom portion of the gas cylinder is formed with a central opening, an upwardly directed engaging member extends about a periphery of said opening, so as to slidably engage the exterior portion of said hydraulic cylinder.

20. The prosthetic device according to claim 11, wherein said bottom portion of the gas cylinder and said plunger are made of a semi-resilient material and are capable of being spring loaded.

21. The prosthetic device according to claim 11, wherein said piston is connected to said upper prosthetic limb member by a connecting element, said connecting element passes through and is fixedly connected to said top portion of the gas cylinder.

* * * * *